United States Patent [19]

Sanderson et al.

[11] 4,247,517

[45] * Jan. 27, 1981

[54] STERILIZED STORAGE CONTAINER

[75] Inventors: Roger S. Sanderson, 24772 Santa Clara, Dana Point, Calif. 92629; Robert C. Whelchel, Newport Beach, Calif.

[73] Assignee: Roger S. Sanderson, Dana Point, Calif.

[ * ] Notice: The portion of the term of this patent subsequent to Apr. 17, 1979, has been disclaimed.

[21] Appl. No.: 895,239

[22] Filed: Apr. 10, 1978

Related U.S. Application Data

[63] Continuation-in-part of Ser. No. 821,042, Aug. 1, 1977, which is a continuation-in-part of Ser. No. 734,228, Oct. 20, 1976, abandoned, which is a continuation-in-part of Ser. No. 703,044, Jul. 6, 1976, Pat. No. 4,196,166, which is a continuation-in-part of Ser. No. 640,824, Dec. 15, 1975, abandoned.

[51] Int. Cl.³ .......................... A61L 2/06; A61L 2/26; B65D 81/20; F16K 31/126
[52] U.S. Cl. ...................................... 422/26; 53/167; 53/425; 206/1.5; 206/204; 206/524.8; 215/260; 215/311; 220/201; 220/208; 220/209; 220/363; 220/366; 220/DIG. 19; 422/40; 422/107; 422/112; 422/293

[58] Field of Search ...................... 21/56, 78, 91–100, 21/104; 49/2, 21, 463; 53/11, 167, 425; 141/301; 206/204, 438, 524.8, 1.5, 439; 215/260, 311; 220/201, 203, 208, 209, 304, 363, 366, 87, DIG. 19; 236/92 R; 251/144, 61.1; 422/25–27, 40, 107, 112, 293, 296

[56] References Cited

U.S. PATENT DOCUMENTS

| | | | |
|---|---|---|---|
| 2,024,511 | 12/1935 | Darling | 220/366 |
| 2,092,445 | 9/1937 | Doulgheridis | 215/355 |
| 2,097,585 | 11/1937 | Carson | 236/92 R |
| 2,489,989 | 11/1949 | Totman | 220/203 |
| 2,997,397 | 8/1961 | Doulgheridis | 215/355 |
| 3,061,196 | 10/1962 | Bauerlein | 251/144 |
| 3,331,105 | 7/1967 | Gordon | 24/16 PB |
| 3,697,223 | 10/1972 | Kovalcik et al. | 21/83 |
| 4,051,973 | 10/1977 | Botkin | 215/260 |

FOREIGN PATENT DOCUMENTS 1642161  8/1970  Fed. Rep. of Germany ............. 21/104

*Primary Examiner*—Bradley R. Garris
*Attorney, Agent, or Firm*—Knobbe, Martens, Olson, Hubbard & Bear

[57] ABSTRACT

A container lid is released at a desired point in a sterilizing cycle with the actuating movement being provided by an expandable chamber having a quantity of sterilizing environment captured during the sterilizing cycle.

22 Claims, 22 Drawing Figures

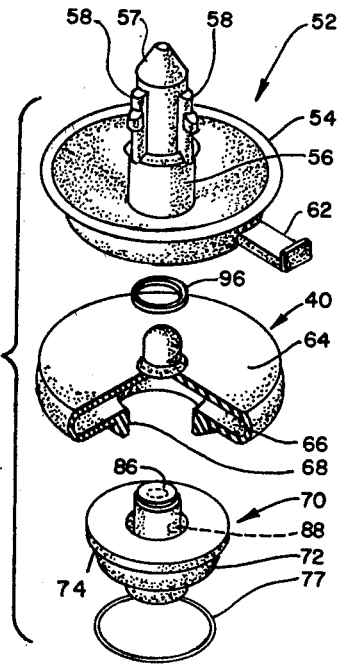
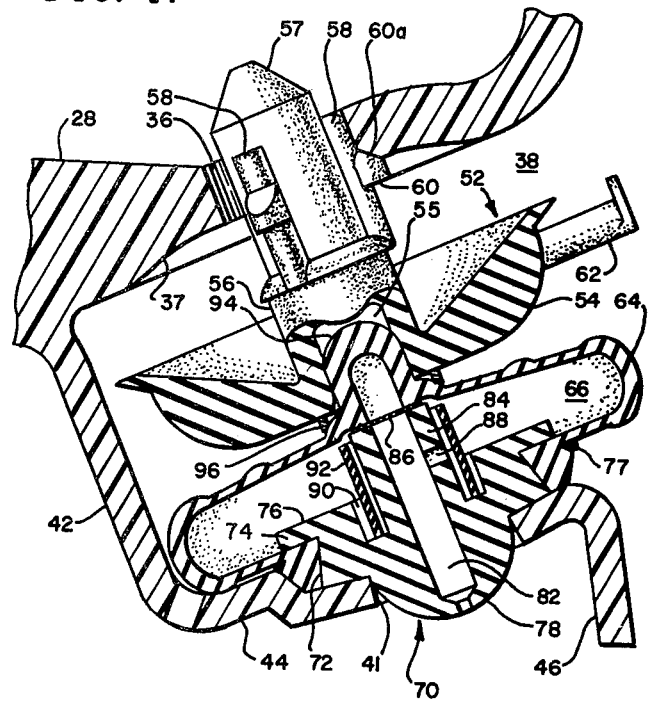
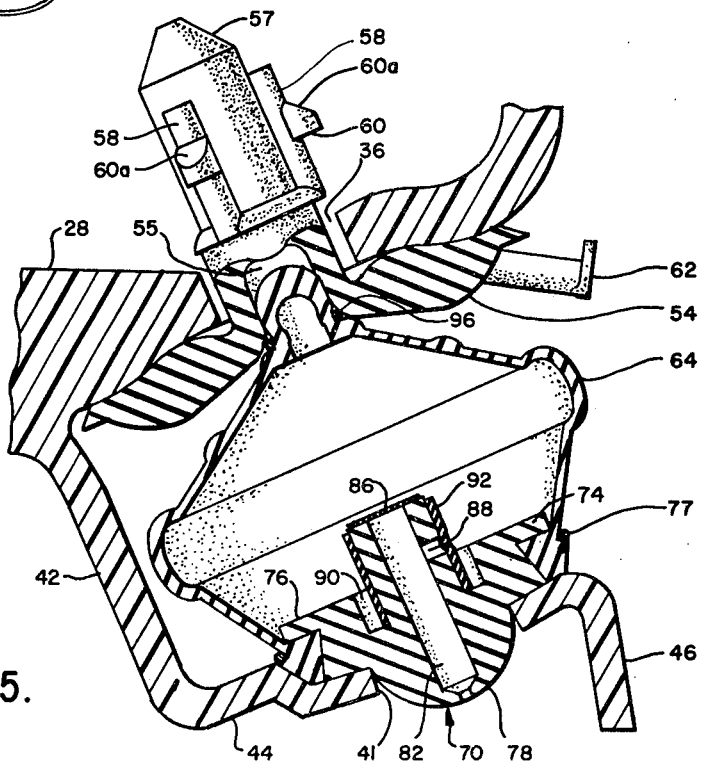
FIG. 4.
FIG. 3.
FIG. 5.

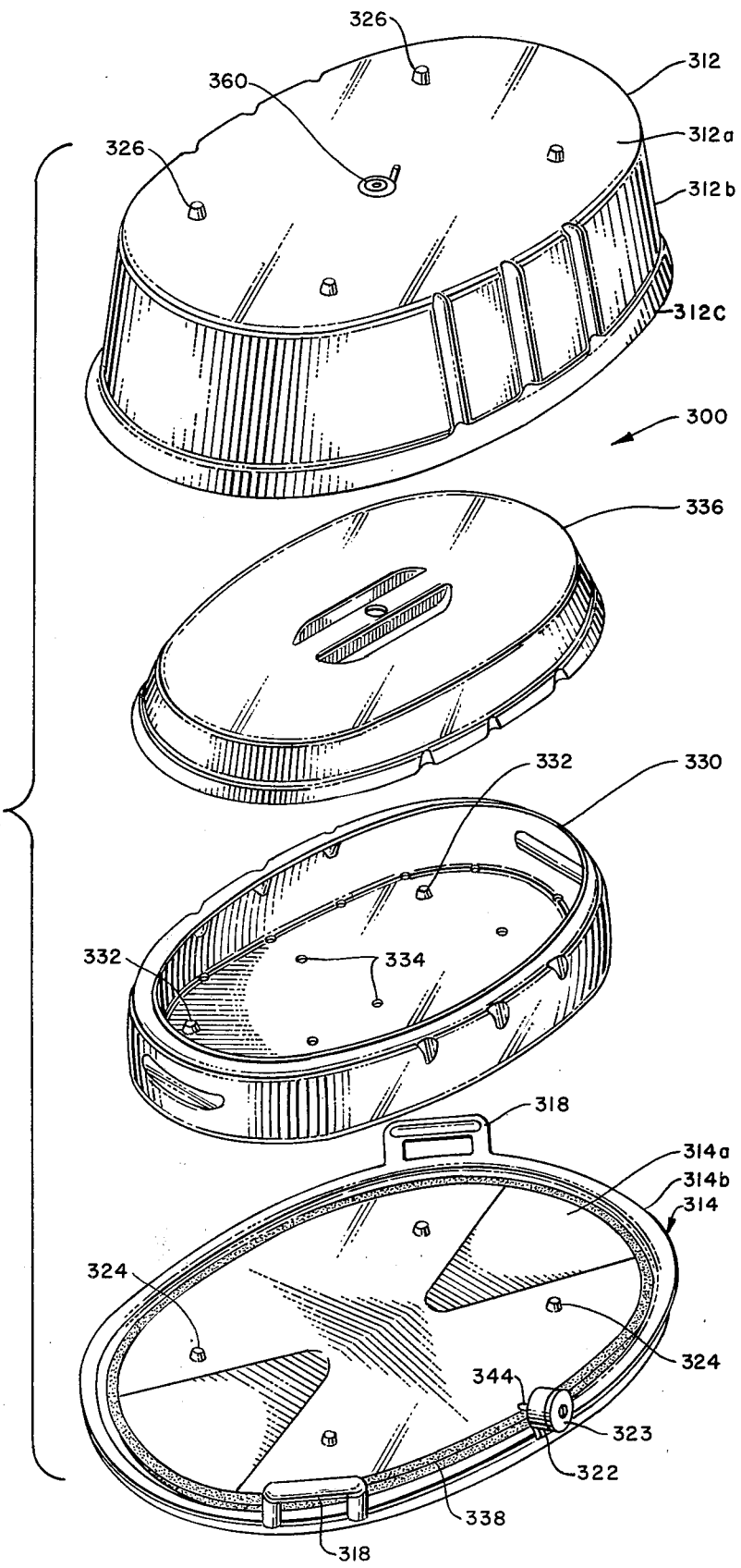

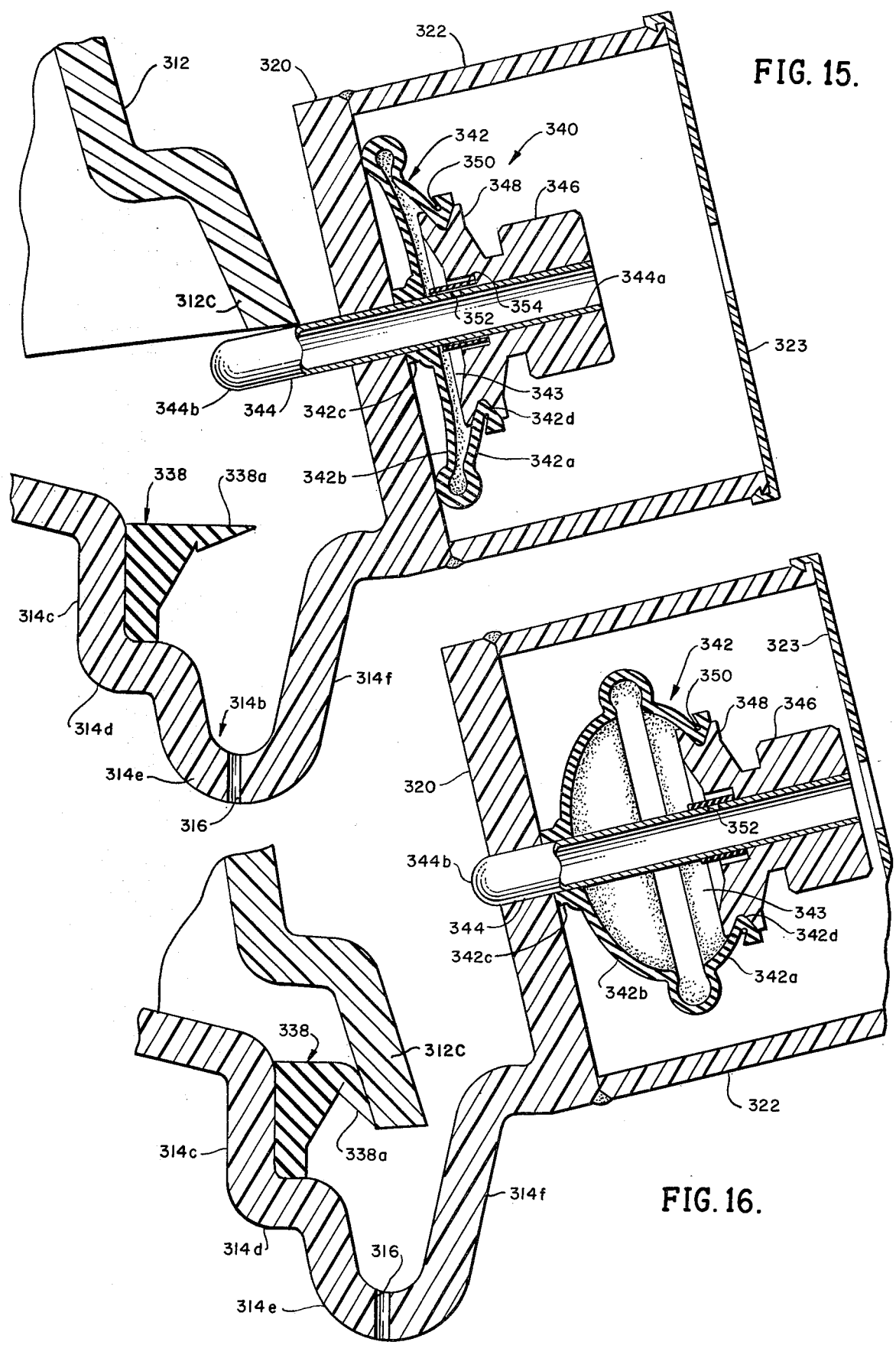

STERILIZED STORAGE CONTAINER

RELATED APPLICATIONS

This invention is a continuation-in-part of U.S. patent application, Ser. No. 821,042, filed Aug. 1, 1977, which is a continuation-in-part of U.S. patent application, Ser. No. 734,228, filed Oct. 20, 1976, which was abandoned in favor of continuation application Ser. No. 923,359, filed July 10, 1978 and which is a continuation-in-part of U.S. patent application, Ser. No. 703,044, filed July 6, 1976, which issued as U.S. Pat. No. 4,196,166 on Apr. 1, 1980, which is a continuation-in-part of application Ser. No. 640,824, filed Dec. 15, 1975, which was abandoned in favor of continuation application Ser. No. 827,992, filed Aug. 26, 1977 now U.S. Pat. No. 4,149,650, issued Apr. 17, 1979.

BACKGROUND OF THE INVENTION

This invention relates to an improved system for storing items while they are being sterilized, while they are being stored awaiting use, while they are in the process of being used, and after they have been used and are awaiting resterilization. The system is particularly useful in connection with the sterilization and storage of medical items, such as surgical instruments.

The most commonly used method for sterilizing surgical instruments and other medical items is to place them in towels which are enclosed in a sheet and taped shut for placing in a sterilizing autoclave. Sterilizing steam applied to the interior of the autoclave penetrates the porous materials surrounding the items to be sterilized. Moisture is removed by a vacuum drying cycle within a vacuum autoclave. When pressure is then returned to normal by admitting room air, unsterile air and lint from the towels are drawn into the center of the package. When the package is removed from the autoclave and cooled, additional room air circulates into the package. Thus, the items are immediately contaminated to some extent. If the package is not used immediately and placed in storage for a period of time, it must be returned to the autoclave for resterilization. It is estimated that two-thirds of sterilization work load in many hospitals is for items that were not used within the shelf life of the pack. This of course is an expensive and inefficient procedure which adds to the skyrocketing costs of medical treatment. Thus, a need exists for a practical and reliable system for handling sterile items and for maintaining sterility.

The above-referenced patent applications and two earlier patent applications, Ser. No. 710,521, filed Aug. 2, 1976 and Ser. No. 710,522, filed Aug. 2, 1976, now U.S. Pat. No. 4,105,407 in the name of Roger S. Sanderson disclose containers in which the items to be sterilized are placed within the container and the container is then placed within an autoclave or other sterilizer. The container is initially sufficiently open to permit the sterilizing environment to circulate within the interior of the container and the container is then sealed at an appropriate stage to maintain sterility. Further, the container in the earlier joint inventor cases is constructed such that steam can escape or be withdrawn from the container when the pressure on the interior of the container exceeds the pressure on the exterior. Consequently, the container is usually essentially dry with a vacuum type autoclave wherein a vacuum is applied to the container at the end of the steaming cycle. Also, only a slight amount of moisture remains in the container with a gravity-type autoclave for most sterilizing operations, and this moisture can be absorbed by a small quantity of dessicant.

However, in U.S. application, Ser. No. 821,042, referred to above, it is explained that with loads involving a considerable mass, such as a large quantity of surgical instruments, steam must be circulated through the autoclave for a considerable period of time to heat the load to the necessary sterilizing temperature. During this operation a considerable amount of steam condenses on the colder metal. Although this condensate is eventually sterilized in the autoclave, it is desirable that the container in which the load is stored be as dry as possible. In that application a container is provided and claimed having a valve in its lower wall which remains open until the pressure drops at the end of a steaming phase of a sterilizing cycle. Consequently, any condensate occurring drains from the container through the open valve.

The valve closing means includes an inflatable chamber which is initially open to high pressure steam in an autoclave, and is then automatically closed in response to the steam temperature, capturing a quantity of high pressure steam within the expandable chamber. This steam causes the chamber to expand at the end of the steaming phase of the cycle when there is a significant pressure drop. The force created by the expanding chamber is employed to close the valve in the container wall.

The container lid, gasket and base are constructed such that residual steam can be withdrawn from the container even after the valve is closed when the pressure on the exterior of the container is less than the pressure on the interior of the container. Moreover, when the pressure on the exterior is increased, this pressure holds the valve in closed position and draws the lid more tightly on the base.

SUMMARY OF THE INVENTION

The present invention discloses the arrangement in application, Ser. No. 821,042 for background purposes and another arrangement wherein an inflatable chamber-type actuator is employed to ensure that a container is held open until after the end of the steaming phase to permit condensate to drain from the container and the container is then automatically closed. More specifically, in this arrangement, the container is formed with a generally flat base having no side walls, with the center of the base being raised slightly from the periphery so that condensate can flow to the edge of the container. The lid, which includes a top wall and depending side walls, cooperates with the base to close the container. The lid is initially held open on one side by an element extending between the lid and the base. The element is connected to be withdrawn by the force produced by an expandable chamber, which expands as the pressure drops within the autoclave at the end of a pressure steaming phase. Thus, instead of the expandable chamber closing a valve, it simply releases the lid and allows it to fall into position. A simple, separate relief valve is provided for relieving the vacuum later formed in the container, to permit opening of the container.

In a preferred form of the invention, the element holding the lid open is a pin which is connected to one end of a generally disc-shaped expandable, balloon-like chamber, with the pin extending through the chamber and out the other end. The chamber is positioned against an upwardly extending support on the periphery of the base with the pin extending through a hole in the support to hold the lid spaced from the base. Thus, when the chamber expands, the end of the chamber which is connected to the pin moves away from the base, withdrawing the pin from its lid supporting position.

The expandable chamber actuator is constructed so that the lid is allowed to close before the pressure within the autoclave or other sterilizer reaches ambient pressure. This ensures that the lid is closed before any unsterilized air is allowed to enter the autoclave at the completion of its cycle. This provides complete sterility with either a vacuum-type autoclave, wherein a final vacuum is applied after the end of the steaming phase, as well as with a so-called gravity-type autoclave wherein a final vacuum is not applied.

While this arrangement provides the desired result and is necessary with present-day technology, a significant cost saving can be made in the construction of the container if the air entering the autoclave at the end of the final vacuum in a vacuum-type autoclave would be sterile. With present-day autoclaves, the manner by which pressure is equalized in the autoclave at the end of the final vacuum is simply to open a valve which permits filtered outside room air to enter the autoclave. Although the filter provides some degree of sterility, it does not provide the level of sterility which is desired to minimize the possibility of contamination within the container. Consequently, the presently preferred approach is to cause the container to close as the autoclave pressure is falling but before it reaches its lowest pressure. Nevertheless, since the container lid, base and gasket are constructed to permit fluid flow out of the container even after the container is closed, a very high vacuum is attained within the container, particularly in a vacuum-type autoclave. Because of this, it is naturally necessary that the container be constructed to withstand such high vacuum. For a variety of reasons it is desirable to utilize transparent plastic to form the container; and hence, it is necessary that the walls be relatively thick to withstand the pressure. If in the future autoclaves are provided which include a filter that essentially sterilizes the air which is introduced into the autoclave at the end of the cycle to equalize pressure, it would not be necessary to close the container before the low pressure point during the final vacuum of an autoclave cycle; but instead, the container could be closed during the time the pressure is rising from the low point, since the air being introduced to equalize pressure would be sterile. It would only be necessary to have the counter closed before it is removed from the autoclave and exposed to unsterile air. Closing the container with a lesser vacuum existing within it would lower the strength requirements for the container so that the walls could be made thinner. This of course would result in a substantial savings of material.

Thus, another embodiment of the invention, there is provided a mechanism which holds the container open until the pressure is rising after the maximum vacuum point is reached during the final vacuum phase of an autoclave cycle. This mechanism employs the inflatable chamber means disclosed in application, Ser. No. 821,042, as an actuator to automatically control the closing of the container. The expansion of the chamber is used to trigger a two-step closing operation, and the later contraction of the chamber as pressure surrounding the chamber increases, causes closing of the container.

In a preferred arrangement of this two-step closing process, a lever is pivotally mounted on the periphery of the container base with one end of the lever extending between the lid and the base to hold initially the lid spaced from the base. A spring urges the lever into that lid holding position. As the pressure drops at the end of the steaming phase of an autoclave sterilizing cycle, an inflatable chamber expands in the manner discussed above, and the chamber is positioned so that its expansion provides a force which pivots the lever to withdraw the end of the lever which is initially supporting the lid. However, this pivoting movement simultaneously causes the other end of the lever, or a pin attached to it, to move beneath the lid so that when the lid falls from the support provided by the first end of the lever, it only falls a small amount so that it is still retained by the other end of the lever. The inflatable chamber continues to expand until the maximum vacuum condition is reached; however, as outside filtered air is then admitted to the autoclave, the increasing pressure surrounding this sealed inflatable chamber causes the inflatable chamber to once more contract. This in turn permits the lever to be once more pivoted in response to the urging of the spring and withdraw the second end of the lever which had been supporting the lid. Consequently, the lid falls into closed position. The point at which the lid finally closes may be easily predetermined as desired by controlling the length of the pin or second end of the lever which supports the lid. Thus, it can be seen that the improvements described herein provide versatility to insure complete sterility with present-day sterilizing equipment and yet are readily adaptable to improvements which may occur in such equipment.

For a more thorough understanding of the invention, refer now to the following detailed description and drawing in which:

FIGS. 1–13 disclose the improvements that are set forth in the above-referenced application, Ser. No. 821,042 to provide background information in describing the improvements of the present invention; thus, FIG. 1 is a perspective view of the container of the earlier invention;

FIG. 3 is an exploded perspective view of the container valve and valve closing mechanism;

FIG. 4 is an enlarged cross-sectional view of the container valve and valve closing mechanism shown on the container before being actuated by the sterilizing cycle;

FIG. 5 is a cross-sectional view of the structure of FIG. 4 after the valve has been moved into sealing position on the container valve seat by the expandable chamber forming the valve closing mechanism;

FIG. 14 is an exploded perspective view of a preferred form of the container of the present invention;

FIG. 15 is an enlarged cross-sectional view of the actuator mechanism shown in FIG. 14 showing the mechanism in its initial condition wherein it is supporting the lid spaced from the base of the container;

FIG. 16 is a view similar to that of FIG. 15 but showing the expandable chamber expanded so that the pin is withdrawn and the lid is in its closed position;

Figure 17:
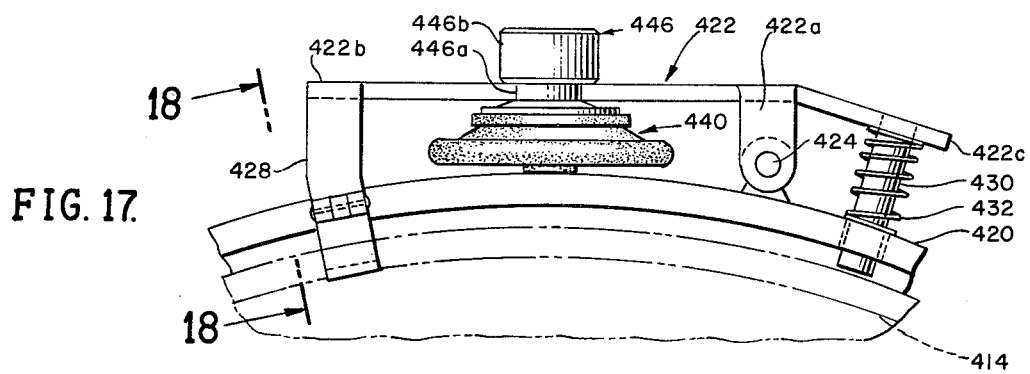
FIG. 17 is a partial plan view of an embodiment of the invention illustrating the mechanism which does not permit the container to close until the pressure is rising after a final vacuum in a sterilizing cycle.
Figure 19:
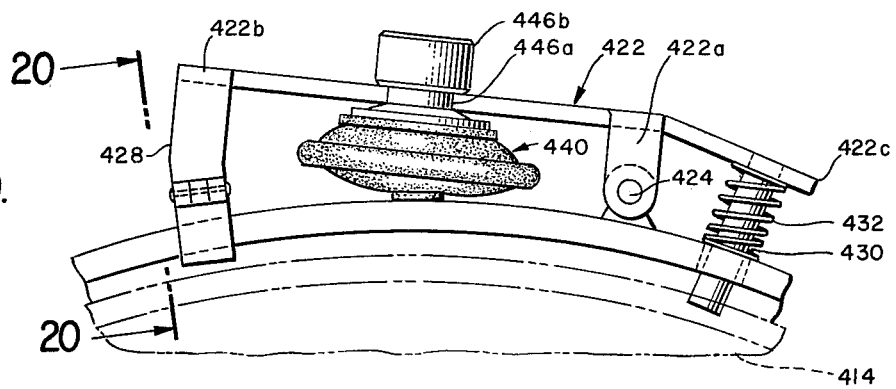
Figure 21:
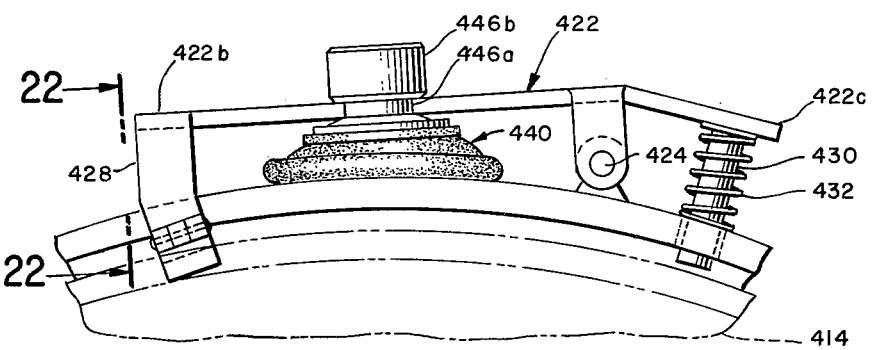
Figures 18, 20, 22:
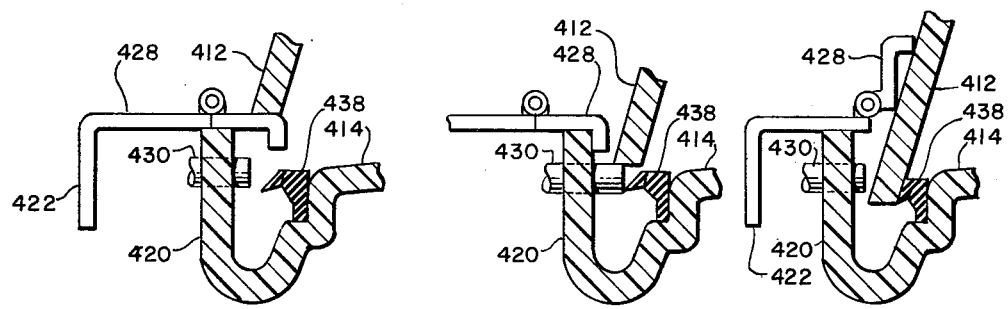
FIG. 18 is a cross-sectional view on lines 18—18 of FIG. 17, showing the lid being supported by one end of a lever.

FIGS. 19 and 20 are respectively similar to FIGS. 17 and 18 with the expandable chamber expanded and the other end of the lever supporting the lid in the open position; and FIGS. 21 and 22 are similar to FIGS. 17 and 18 respectively with the inflatable chamber deflated and with the lid in a closed position.

Figure 1:
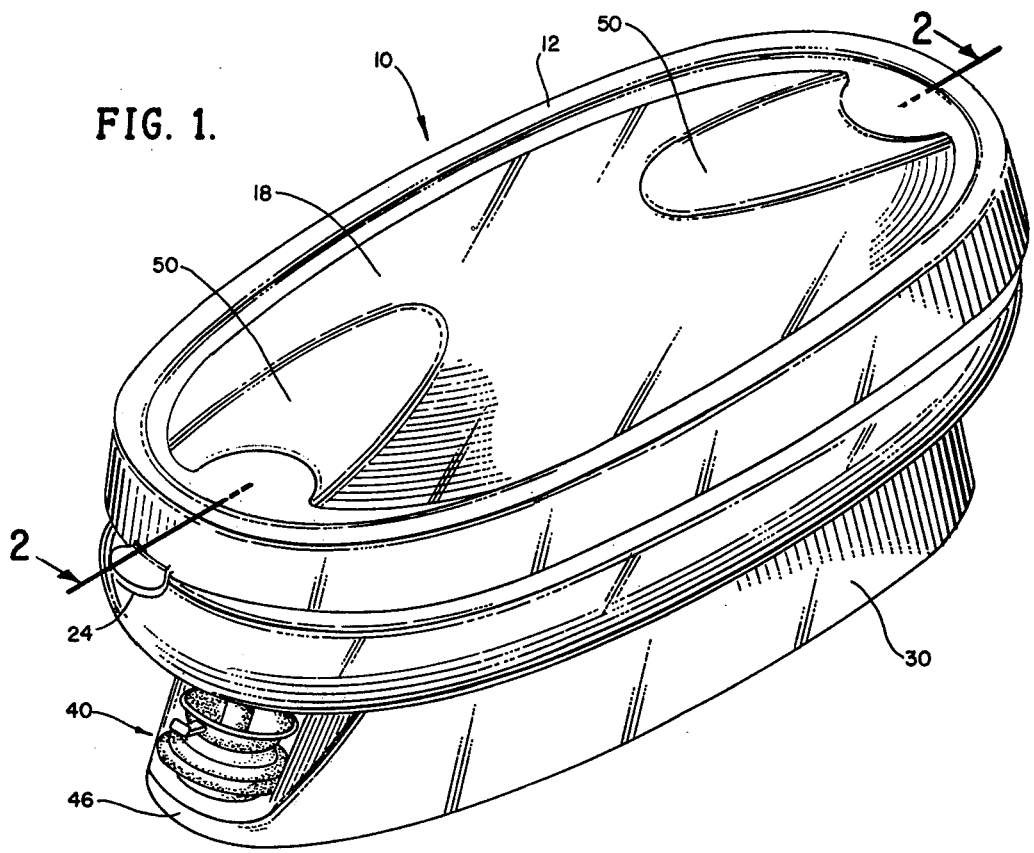
Figure 2:
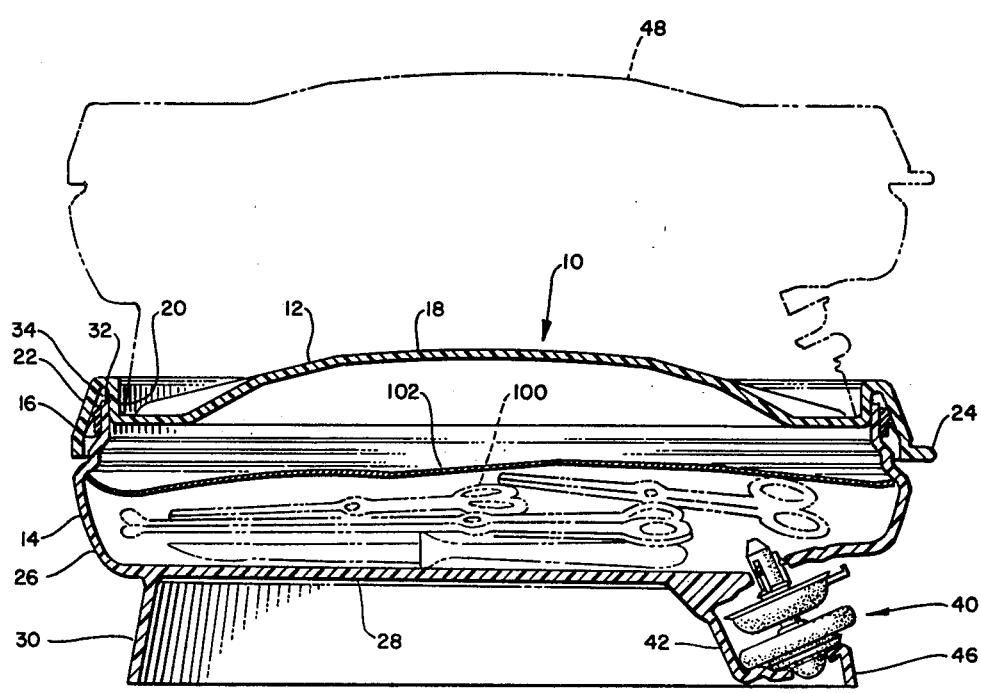
FIG. 2 is a cross-sectional view of the container on lines 2—2 of FIG. 1 illustrating the overall arrangement and the slope of the bottom wall of the container.

Referring now to FIGS. 1 and 2, there is shown a container 10 having a cover or lid 12 closing the open upper side of a base 14 and seated on a gasket 16 extending between the base and the lid. As can be seen, the container has a generally oval or race track configuration and the lid has an upper wall 18 which slopes gradually upwardly towards the center. The purpose for the oval shape and the upwardly curving wall 18 is to provide strength to the container when it is subjected to an exterior pressure considerably higher than the interior pressure. The cover 12 further includes a peripheral flange portion having a generally vertical internal wall 20 which joins at its upper end a downwardly and outwardly sloping flange 22. A tab 24 extends outwardly from the bottom of the flange 22 at one end of the container.

The base 14 includes an irregular but generally upwardly extending side wall 26 formed integral with a bottom wall 28 and a downwardly extending peripheral leg structure 30. The side wall 26 terminates at its upper end with a short vertically extending portion 32 which extends into the downwardly extending groove 34 formed by the inner surface of the lid flange 22 and the outer surface of the lid wall 20. As can be seen from FIG. 2, the lid wall 20 fits within the upper end of the base wall 32. The portion of the side wall 26 below the upper portion 32 extends outwardly to a point where the lower portion of the wall 26 generally aligns with or forms an extension of the exterior surface of the lid flange 22.

The gasket 16 is made of flexible rubber-like material which can withstand the temperatures of an autoclave operation and yet provide an adequate seal. The gasket 16 includes an inner vertical portion which fits snuggly around a groove in the wall 32 on the upper end of the base side wall 26. The gasket 16 further includes a downwardly and outwardly extending flange portion which mates with the inner surface of the lid flange 22.

The bottom wall 28 of the base slopes generally toward a valve opening 36 in the right end of the base as viewed in FIG. 2. The base leg 30 extends inwardly at the right end of the base to form a recess 38 in which is positioned a valve and valve closing assembly 40 which cooperates with the valve opening 36. More specifically, the recess 38 is formed by a sloping leg wall 42 which extends in a generally cylindrical configuration about 180 degrees to partially enclose the valve and valve closing assembly 38. The wall 42 is further connected to a bottom support wall 44 which extends generally perpendicular to the side wall 42 and joins with a stub leg wall 46 on the periphery of the base leg. A hole 41 is formed in the bottom wall 44 for positioning the assembly 40.

As can be seen by the broken lines in FIG. 2, a second container 48 may be stacked on the lower container 10 with the leg of the upper container being positioned on the lid 12 in the groove formed by the lid side wall 20 and by the outer periphery of the lid upper wall 18. As seen from FIG. 1, each end of the lid has a shallow recess 50 adapted to receive the wall portions 44 and 42 of the upper container 48. A recess 50 is formed on each end of the lid so that the user need not worry about orientation of the container 48 when it is being stacked on the container 10. Naturally more than two containers may be stacked if desired.

Referring now to FIGS. 3 and 4, the valve and closing mechanism 40 may be seen to include a valve 52 which is a flexible resilient member molded of silicone rubber or other rubber-like material which can withstand steam temperatures while maintaining its resiliency. The valve includes a base 54 which when unrestrained has a generally saucer-shaped configuration with the upper surface of the base 54 forming the sealing surface against the container when the valve is closed. Attached to the central portion of the base 54 is an upwardly extending generally cylindrical stem or core 56. As may be seen from FIGS. 4 and 6, much of the core 56 is hollow opening to the lower side of the base 54. The upper end of the core 56 extends through the opening 36 in the container lower wall, the end 57 of the core 56 having a solid conical shape to facilitate insertion of the core into the opening 36. The portion of the core 56 actually extending through the opening 36 as viewed in FIG. 4 includes three radially extending circumferentially spaced ribs 58. Each rib further has a radially extending lug 60 which has a tapered upper surface 60a which engages the lower edge of the opening 36 with the assembly positioned as shown in FIG. 4.

A tab 62 extends radially outwardly from one edge of the valve member base 54 to form a convenient element for removing the valve member from the valve opening 36.

The assembly 40 further includes a valve closing means comprising a generally disc-shaped hollow member 64 which is made of flexible rubber-like material and defines an expandable interior chamber 66. Since the member 64 is flexible and stretchable, it might be thought of as a balloon or bellows-like member. The bottom side of member 64 includes a centrally located thickened throat 68 which defines a circular opening into the chamber 66. A circular plug 70 snaps within the throat 68 in the lower wall of the member 64. More specifically, the plug 70 includes a side wall 72 which slopes downwardly and outwardly and is slightly larger in diameter than the throat 68. A side wall 72 further includes an outwardly extending flange 74 that forms a continuation of the upper wall 76 of the plug. The throat 68 snuggly engages the side wall 72 of the plug and the flange 74 snuggly engages the lower wall of the chamber 66 surrounding the throat 68. While the plug 70 snaps into position in the throat 68 to close the chamber 66, there is further provided a resilient ring shaped retaining element 77, which surrounds the exterior of the throat 68 holding it in tight engagement with the plug side wall 72.

The plug 70 further includes a lower guide portion 78 having a curved exterior which fits within an opening 41 in the container wall portion 44 which supports the valve and valve actuating assembly 40.

A valve passage 82 extends centrally through the plug from the lower portion 78 and upwardly into a tubular portion 84 that extends above the upper wall 76. The upper end of the tube 84 is closed by a plate or wall 86. A hole 88 extends radially through the tube 84 to place the chamber 66 in fluid communication with the atmosphere around the assembly 40.

Formed in the upper wall 76 of the plug 70 is an annular recess or groove 90 in which is positioned a thin band 92 which surrounds the tube 84 and extends over the valve opening 88. The band 92 is made of heat shrinkable material which shrinks and becomes permanently rigid at a predetermined temperature.

The balloon member 64 further includes an upwardly extending nipple 94 which snuggly fits within the cylindrical recess 55 in the lower wall of the valve base 54 as seen in FIG. 4. The interior of the nipple 94 is hollow and is open to the chamber 66 when the chamber is expanded; however, in the position of FIG. 4, the upper wall 86 of the tube 84 of the plug 70 engages the lower end of the nipple 94 and thereby limits the contraction of the chamber 66. Loosely surrounding the nipple 94 is a heat shrinkable band 96.

OPERATION OF EMBODIMENT OF FIGS. 1-7 IN A VACUUM AUTOCLAVE

Referring to FIG. 2, the container lid 12 is removed and the articles 100 to be sterilized are placed within the base 14. They are then loosely covered by a thin sheet of transparent plastic material 102 which can withstand sterilizing steam temperatures. The lid 12 is then loosely placed in position on the base 14 with the interior of the inner surface of the flange 16 engaging the outer surface of the flexible gasket 22. In this position, the lid or cover is closed in the sense that air cannot flow into the container passed the gasket but the cover is not fully closed onto the base.

A valve and valve closing assembly 40 is positioned within the recess 38 as shown in FIGS. 2 and 4. The components of the assembly 40 are usually provided in an assembled condition wherein the band 96 is first loosely positioned on the nipple 94 of the valve actuating member 64 and the nipple is then pressed into the recess 55 in the lower end of the valve member. The valve is retained in this position by a slight friction fit. The assembly 40 is therefore inserted into the recess 38 as a unit. Since the components are flexible, the upper end 57 of the valve core may be easily inserted into the container valve opening 36, allowing the lower end of the valve actuating member 64 to be snapped into position. The lower surface 78 of the core 70 conforms to the hole 41 in the container support wall 44 to properly align the assembly. The alignment ribs 58 on the valve core 56 properly align the valve with respect to the hole 36. Also, the outwardly extending lugs 60 limit the inward movement of the valve to tell the user of the equipment that the assembly is properly positioned. The tolerance of the components are relatively loose but yet the design is such that precise alignment is not critical to obtain proper seating of the valve.

Figure 8:
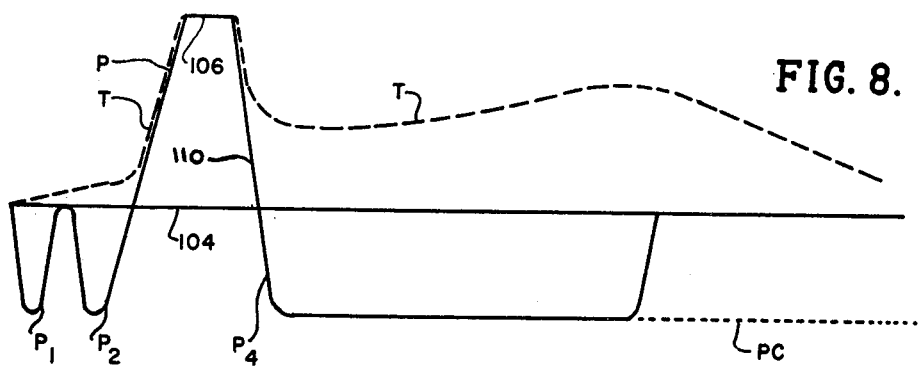
FIG. 8 is a schematic illustration of a vacuum autoclave cycle indicating the points on the pressure and temperature curves at which the operation of the mechanism curves.

The valve closing assembly is primarily designed for use in a sterilizing apparatus which includes a high pressure steam cycle. Two widely used sterilizers are the so-called gravity autoclave and the vacuum autoclave. An example of the pressure and temperature cycles in one type of vacuum autoclave is illustrated in FIG. 8. The horizontal line 104 represents time. T represents a temperature curve and P represents the pressure curve, with the line 104 indicating normal room temperature and pressure. When the container 10 is placed within the vacuum autoclave, a first vacuum environment indicated by the section PI of the pressure curve is first applied. Most of the unsterilized air within the autoclave is withdrawn as is the air within the container 10 since the interior of the container is in communication with the interior of the autoclave by means of the valve opening 36 in the bottom wall of the container. The pressure within the autoclave is then once more allowed to return to ambient pressure by allowing steam into the chamber. A second vacuum cycle P2 on the pressure curve shown on FIG. 8 is then applied which withdraws the steam within the autoclave which has mixed with the small amount of remaining unsterile air. In some sterilizers, additional vacuum cycles of this type are employed.

High pressure steam is then introduced into the autoclave causing the pressure as well as the temperature to rise as indicated by the curves T and P. The temperature and pressure curves are shown coincident at this time in that they both rise at the same time and the units of measurement employed are assumed to cause the curves to move in a coincident manner. It should be understood that this is not intended to be a precise showing of the actual curves but only to illustrate that the temperature and pressure are both rising to their maximum levels during this phase. The high temperature steam of course circulates into the interior of the container by way of the valve opening 36. Also, the high pressure high temperature steam also circulates into the chamber 66 by way of the valve passage 82 and the valve opening 88, noting that the cylindrical valve element 92 is spaced from the opening 88 to permit such flow. Note that even if the valve band 92 is positioned loosely over the opening 88, the pressure differential between the chamber 66 and the surrounding autoclave pressure causes the steam to flow into the chamber 66.

When the temperatures and pressures are near their maximum, the heat of the steam causes the heat shrinkable sleeve 92 to shrink to its position shown in FIG. 5 wherein it closes the opening 88, thereby capturing a volume of high pressure high temperature steam within the chamber 66. This point 106 is shown in FIG. 8.

The steaming cycle continues for a desired period of time. Most autoclaves are adjustable to vary the duration of the steaming portion. The graph shown in FIG. 8 illustrates the steaming cycle to be of relatively short duration; however, the duration should be adjusted to fit the load within the container. A load requiring a particularly long period of time is one which includes a large quantity of metal elements having considerable mass. For example, a large quantity of surgical tools would have considerable mass. Even more demanding, during the testing of the container, a load of steel bolts were placed in the unit. Such a load requires a considerable period of time for adequate sterilizing in that it takes a considerable quantity of steam to heat the entire mass of the load to the desired sterilizing temperature. The surface of the heavy metal items will remain relatively cool until the interior of the items are heated because of the conductivity of the material. As the hot steam strikes the cooler metal, some of the steam condenses and drips onto the floor or bottom wall 28 of the container. Although this liquid would be sterile at the end of a sterilizing cycle, it is desirable that the water be removed from the container so that the container will be as dry as possible during storage. It is for this reason that the bottom wall 28 of the container is slightly sloped so that the water will flow towards and out the opening 36. Regardless of the length of the steaming cycle, the valve 36 will remain open in that there is no force for closing it. However, when the steaming cycle is interrupted, the pressure quickly drops as illustrated by the section P4 of the curve. A final vacuum cycle is then applied to withdraw the steam as indicated by the curve section P4. Following this, the vacuum is removed by allowing the introduction of filtered exterior air so that the pressure within the autoclave returns to room pressure.

As the pressure in the autoclave is dropping from its maximum, the captured pressure within the chamber 66 causes the balloon 64 to expand. Since the pressure drops rapidly into a vacuum phase, the balloon 64 expands quickly into the condition shown in FIG. 5 wherein the nipple portion 94 may be seen to have moved upwardly a considerable distance thrusting the valve member 54 against the annular valve seat 37 surrounding the valve opening 36. As can be seen from FIG. 5, a large portion of the inner upper surface of the flexible resilient base portion 54 of the valve engages the valve seat 37 to form an excellent seal. Note also that the valve seat 37 has a concave configuration or curves inwardly towards the interior of the container and that the valve member conforms to the valve seat surface. The exact point of closure of the valve is not critical but the valve will typically close in the area indicated by the point 110 on the pressure curve in FIG. 8.

It should be noted from FIG. 5 that the balloon member 64 is constructed to insure its expansion into the configuration illustrated. That is, the outer edge walls of the member 64 are somewhat thicker then some of the adjacent portions so that the balloon does not expand radially. Also, the upper wall of the member 64 includes a thickened annular rib portion which causes the balloon to take the general configuration illustrated which insures that adequate upward thrust of the valve closing member is obtained.

It should also be noted that sufficient thrust is required to force the lugs 60a on the valve core 56 through the opening 36. The purpose for these lugs in addition to initially properly positioning the valve is to make sure that the valve does not close prematurely due to a temporary drop in the pressure of the steaming cycle. That is, it has been found that some autoclaves have a considerable pressure variation as the steam is fed through the unit. Thus, a drop in pressure in the middle of the steam phase could cause the valve to close. However, the presence of the lugs 60 requires a sufficient force that normal variations in the steam pressure will not close the valve. About a 10 psi pressure drop is required to close the valve.

Although the container is now closed by virtue of the valve 54 and the gasket 16, recall that the lid 12 was initially only loosely positioned on the base. Thus, as the pressure drops during phase and P4 of the pressure cycle, a pressure differential between the interior and the exterior of the container is initiated. However, a unique quality of the gasket is that it will permit leakage out of the container with a relatively small pressure differential. Consequently, the steam that was within the container when the valve closed is still withdrawn from the container by the vacuum cycle. This is highly desirable because it means that the contents of the container are left in a dry and sterile condition. Thus, even at the bottom of the vacuum cycle, the lid 12 is still only loosely positioned on the gasket 16. Nevertheless, the flexible resilient nature of the gasket is such that gas cannot flow into the container. Thus, the gasket during this phase of the cycle essentially acts like a check valve.

When external filtered air is introduced into the autoclave allowing the pressure to return to ambient, the vacuum which was applied to the autoclave still remains within the container, as indicated by the dotted line PC. The gasket 16 and the valve 54 prevent this external air from entering the container. Although such air is filtered it is nevertheless not sterilized and hence, it is important that this air not enter the container to best maintain sterility.

Since the incoming air cannot enter the container, the pressure of this air quickly forces the lid downwardly into its maximum closed position with the lid flange 22 tightly pressed against the gasket 16 so as to more positively prevent external air from entering the container. Similarly, the exterior air presses against the valve member 54 causing it to remain tightly seated on the valve seat 37 as illustrated in FIG. 6.

Referring again to FIG. 8, the temperature in the autoclave also drops rapidly once the steaming cycle is interrupted, but then remains at an elevated level and slightly rises during the final vacuum phase, since the autoclave is heated. When the container is removed from the autoclave, the temperature gradually returns to normal. The reduction in temperature within the autoclave and later outside the autoclave eventually also cools the steam within the balloon chamber 66 causing a reduction in pressure within the chamber 66. This causes the resilient balloon member 64 to contract and revert to a position close to that it originally assumed, as illustrated in FIG. 6. The valve member 54 is of course no longer supported by the balloon 64 in that the ambient pressure is tightly holding the valve in position without any other support. This force is so strong that the weight of the inflatable chamber members 64 and 70 is of no consequence with respect to the seal produced by the valve, but usually the enlargement of the valve recess 55 results in the members following and returning to the position shown in FIG. 6. However, if the friction between the nipple 94 and the tubular recess 55 is sufficient, the valve closing member will be lifted from its seat resting on the support wall 44. The valve closing member may remain in either of these two positions or it may be withdrawn or recycled for an additional use. It can of course, not be reused unless the plug 70 is withdrawn from the flexible member 64 and the heat shrink band 92 removed so that the valve opening 88 once more permits communication between the chamber 66 and the exterior. By providing a new heat shrink band 92, the valve closing member can be reused. Normally, such recycling will be performed by people other than those using the container.

Figure 6:
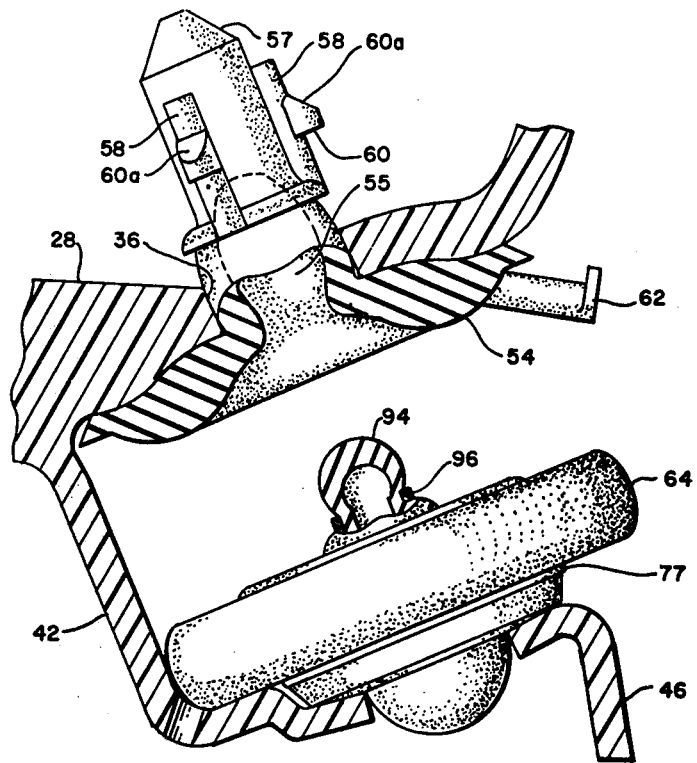
FIG. 6 is a cross-sectional view of the structure of FIG. 4 showing the valve held in place by pressure on the exterior of the container and showing the expandable chamber in retracted position.

Note from FIG. 6 that the heat shrink band 96 has shrunk tightly onto the nipple 94 because of the high temperature steam. This band 96 is colored differently from the nipple 94 to provide an indication to the user of the container that the valve moving member has been used. Thus, this indicator band should be removed when the internal heat shrink valve element is replaced. A new indicator band should be loosely positioned over the nipple when it is inserted in a valve which is to be reused.

Figure 7:
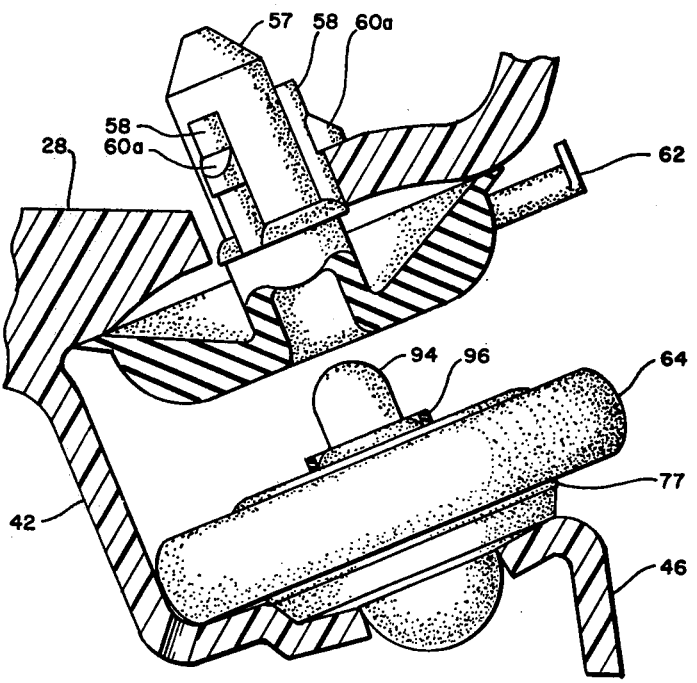
FIG. 7 is a cross-sectional view of the structure of FIG. 4 as it appears after the valve has been placed in position by the expandable chamber near the end of the steaming phase of a gravity autoclave, but before the valve is tightly drawn into sealing position on the container valve seat by the vacuum created in the container as it cools.

With the valve member closing the opening in the end of the container, the contents of the container may be maintained in sterile condition for a long period of time. So long as the valve is in the position shown in FIG. 6, an observer will know that the contents are still sterile. If the vacuum within the container should be lost, the valve will withdraw slightly from the tightly sealed position due to the weight of the valve and its memory. This will tell the observer that the contents may no longer be of maximum sterility. However, the lugs 60 on the valve core 56 continue to hold the valve in the sealed position shown in FIG. 7. While such seal has permitted some air to enter the container as the vacuum was lost, the contents still have a minimum amount of contamination, and it is much less than that which relatively quickly results with present day methods of wrapping items to be sterilized and stored in towels.

When the container is to be opened and the valve is still tightly sealed as shown in FIG. 6, the valve member may be readily removed by pulling on the tab 62 attached to the valve member. As mentioned above, the valve member can be reused if desired, assuming it has not been held in a valve closed position so long that the material no longer has adequate resiliency to maintain its original shape.

The container cover may then be removed, although it may still be somewhat tightly in position even though the vacuum has been removed. To facilitate removal of the cover, the base may be held with one hand and the cover lifted by means of the tab 24 located on one end of the cover.

Normally, the container will have been removed from a storage location into the operating area before it is opened. When the cover is removed, there is a possibility that some dust or other contamination that may have accumulated on the exterior of the cover during storage could drop into the container interior. It is for this reason that the additional barrier layer of flexible plastic 102 was installed over the instruments prior to the sterilizing operation. This barrier layer can now be carefully removed by grasping one end and withdrawing it over one edge of the container so that hopefully any dust that may have fallen into the container will be removed with the barrier layer, or at least such dust will not fall directly onto the sterile instruments.

GRAVITY AUTOCLAVE OPERATION

Figure 9:
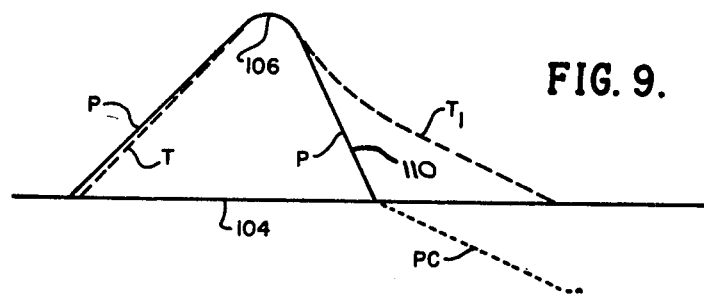
FIG. 9 is a sketch similar to FIG. 8 but for a gravity autoclave.

While a vacuum autoclave sterilizing cycle is preferable from a standpoint of sterility and from a standpoint of best operation of this container, a large number of gravity autoclaves are still employed and the valve and valve closing assembly 40 of this invention can accommodate such cycle as well. Referring to FIG. 9 it may be seen that there are no vacuum cycles applied but instead high pressure steam is simply applied and then withdrawn. The valve and valve closing assembly 40 is used in the same manner as described above in connection with the vacuum cycle. The valve member 54 is closed at approximately the same location 110 on the pressure curve. Also, as the pressure is exhausted from the autoclave, pressure is exhausted from the container passed the gasket in the same manner as described above. However, the only means for creating a vacuum within the container which will draw the lid more tightly into closed position and will hold the valve member 54 in tightly sealed condition is that vacuum which is created as the temperature of the small amount of residual steam within the container drops. The vacuum created in the container will follow a line more proportional to the temperature curve indicated at T1 in FIG. 9. Thus, for a period of time, there may be insufficient pressure differential to hold the valve member 54 in the tightly sealed position shown in FIG. 6. Instead, it may temporarily drop to the position shown in FIG. 7 wherein the lugs 60 retain the valve member in a sealing condition which prevents air leakage into the container. Note that the outer periphery of the valve member is oriented to properly engage the valve seat in that condition to prevent leakage into the container.

As the temperature of the residual steam within the container drops further, an adequate pressure differential is created which will force the valve member back into the tightly sealed condition of FIG. 6. Also, it will pull the lid tightly into a sealed position on the gasket 16. The pressure within the container is indicated by the dotted line PC in FIG. 9. It should be appreciated that a relatively high vacuum is obtained even with the gravity type autoclave simply due to the pressure drop which is created as the residual steam condenses. While it is desirable that the contents of the container be completely dry, a small amount of sterile water, such as a few drops within the container does not present a significant problem.

Figure 10:
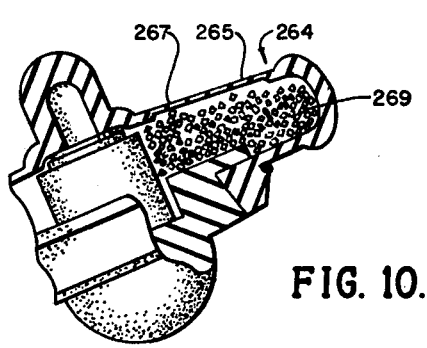
FIG. 10 is a fragmentary view showing a variation of the expandable chamber serving as a dessicant bag.

However, to keep such moisture away from the items in the container, a small amount of dessicant or other moisture absorbing material may be positioned in the container, with suitable means to isolate the dessicant until the end of the cycle. Such an arrangement is shown in FIG. 10 which illustrates an expandable balloon member 264 which is identical to the member 64 in FIG. 4 except that the upper wall 265 has a breakable or rupturable portion 267 which is much thinner than the adjacent wall thickness. The chamber within the member 264 is filled with dessicant which is exposed to the interior of the container at the appropriate time to absorb residual moisture. In use, the inflatable member 264 is filled with a suitable dry dessicant 269 in granule form, which leaves a quantity of air in the chamber surrounding the granules. A plug 70 carrying a heat shrink band 92 like that shown in FIG. 4 is then inserted in the lower wall of the inflatable member 264 in the manner discussed above. The unit is then heated in an oven to sterilize the dessicant and to sterilize the interior of the inflatable member 264. During this heating process, the heat shrink tube 92 will shrink and close the valve opening leading to the interior of the inflatable member 264, capturing a small volume of air that was in the oven. The proper time for sterilization at a given temperature is allowed. The member is then cooled and in effect becomes a small dessicant bomb which will rupture under the proper pressure conditions.

When the container 10 of FIG. 1 is to be used in a gravity autoclave, one of the sealed members 264 filled with dessicant 269 is placed into the container along with the items to be sterilized. When the sterilizing environment is applied to the container, it can not enter the dessicant bomb 269 because it is sealed. However, at the end of the sterilizing cycle, when a vacuum is quickly created in the container as the residual steam in the container is cooled and condenses, the pressure is not reduced as quickly within the member 264 because the air in the member remains gaseous. Consequently, the member inflates or expands as the surrounding pressure within the container falls and the thin wall section 265 will rupture exposing the dessicant to the interior of the container.

Figure 11:
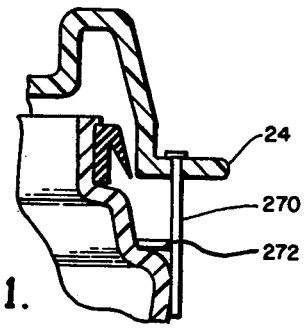
FIG. 11 is a fragmentary view showing another variation of the container in the previous application wherein the lid of the container is initially held open.

Another aspect of using the container in a gravity autoclave is that the container is initially filled with unsterilized air when it is placed in the autoclave. When steam is applied, it mixes with the air and sterilizes it. However, there is some possibility that a pocket of air may be trapped within the container near the end of the container opposite from the valve opening in that the air is heavier than the steam and circulation may not be complete simply by having the valve open. Thus, as a further assist to adequate circulation, there is shown in FIG. 11 the end of the container opposite the valve assembly wherein a heat responsive fuse-like element 270 is shown holding the lid 12 spaced slightly from the base 14. The element 270 is inserted in a hole in the lid tab 24 with an interference fit in a manner to be axially fixed and supported by the lid. A horizontally extending stop 272 on the element 270 and the lower end of the element 270 engage the side wall of the base to hold the lid in the spaced position shown. The element 270 is made of a material which will soften after being subjected to the high temperature steam for a predetermined period of time. Thus, the lid is partially open when steam is first applied with the result that the steam can circulate beneath the lid into the container displacing the air in the container out through the open valve in the bottom of the container. When the element 270 softens, the lid simply falls into its initially closed position as discussed above in connection with FIG. 2; and the remainder of the cycle is as previously discussed. Other similar fuse-like arrangements may be employed for temporarily holding the lid ajar.

FIGS. 12 AND 13

Figure 12:
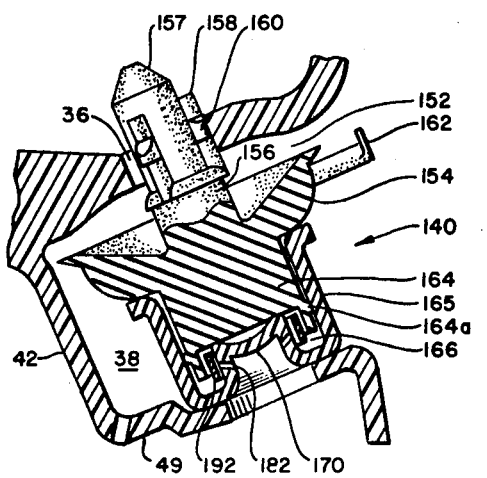
FIG. 12 is a cross-sectional view of a piston-type expandable chamber valve closing mechanism shown before the chamber has expanded to seat the valve.
Figure 13:
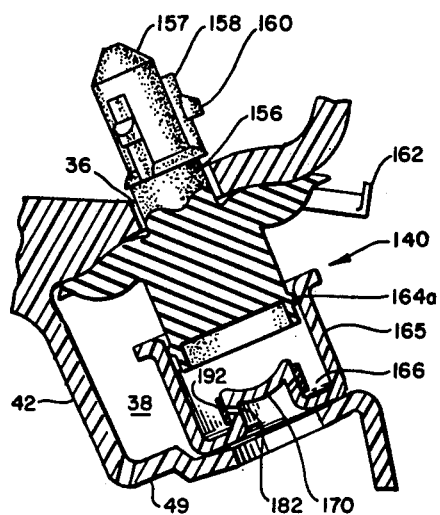
FIG. 13 is an elevational view of the structure of FIG. 12 showing the components after the valve has seated.

FIGS. 12 and 13 illustrate an alternate embodiment of the valve and valve closure mechanism as used in an identical container. Referring to FIG. 12 there is shown a valve and valve closure assembly 140 which includes a valve 152 having a saucer shaped base 154 and a centrally located upwardly extending core or stem 156 having a conical tip 157. Like the valve 52, the core 156 is provided with three ribs 158 having radially extending lugs 160. A tab 162 is formed integral with the base 154 for removing the valve from the valve opening 36.

Also formed integral with the valve base 154 is a cylindrical portion which forms a piston 164. This piston is slidably positioned within a cup shaped member 165 defining a variable or expandable chamber 166 in cooperation with the piston 164. An annular bead 164a on the lower end of the piston engages the walls of the cylinder 165 to form a piston ring.

The cup shaped cylinder has a centrally located inwardly extending portion 170 which limits the movement of the piston 164 into the cylinder 165. One or more valve openings 182 place the chamber 166 in fluid communication with the exterior of the chamber. Surrounding the central portion 170 and the valve openings 182 is a heat shrink band 192 similar to that shown in FIG. 4. As seen in FIG. 12, the band is spaced from the valve openings 182 so that fluid communication into the chamber 166 is maintained.

In operation, the assembly 140 functions essentially like the assembly 40 previously described. The heat band 192 shrinks at a predetermined temperature level indicated at point 106 on the curves in FIGS. 8 and 9. Thus, a quantity of high temperature, high pressure steam is captured within the chamber 166. When the pressure drops within the autoclave, the captured steam in the chamber 166 expands and reacts against the piston 164, forcing it upwardly and outwardly so that the valve 154 is sealed on the valve seat 37 as shown in FIG. 13. As the vacuum is created in the container in the manner discussed above in connection with the two sterilizing cycles, the resulting pressure differential will hold the valve in the seated position shown in FIG. 13.

With the arrangement of FIG. 13 it is intended that the cylinder 165 remain with the container in the position shown. When the container contents are to be used, the valve 152 may be removed in the same manner as the valve 52 namely by pulling on the tab 162.

It should be understood that with either expandable chamber mechanism, a simple check valve is satisfactory for capturing steam in the chamber means for use in a gravity autoclave. Such a valve will permit flow into the expandable chamber but not out. The temperature responsive valve is employed so that in a vacuum autoclave cycle, the chamber does not expand during either of the initial vacuum cycles. The heat shrink bands 92 and 192 actually function as check valves after they initially shrink in that the material is rubber-like at that time. However, when the material later cools, it becomes permanently rigid.

DESCRIPTION OF FIGS. 14–16

The preferred form of the container 300 illustrated in FIG. 14 includes an upper somewhat dome-shaped portion or lid 312 having an upper wall 312a and depending side walls 312b. The lower portion of the side walls 312b flare outwardly and downwardly forming a flange 312c which mates with the base 314 to form a closed container. As may be seen, the base 314 includes a bottom wall 314a which is generally flat, but the central portion of the wall is raised and slopes outwardly to a perhiperal groove portion 314b. As can be seen from FIG. 15, the groove portion 314b includes an upper inner generally vertical wall 314c which extends downwardly from the periphery of the bottom wall 314a. The wall 314c is formed integral with a generally horizontal flange 314d which in turn joins with a U-shaped lower portion 314e. The outer portion 314f of the U-shaped portion 314e extends upwardly and outwardly to about the level of the periphery of the bottom wall portion 314a. A plurality of drainage holes are formed in the bottom of the U-shaped portion 314a, one of such holes 316 being shown in FIG. 15.

The container base 314 is also provided with a pair of handles 318 connected to the groove wall portion 314f. Located on one side of the container base is an upstanding wall or support 320 attached to the outer upper portion 314f of the U-shaped groove 314b. A cylindrical actuator housing 322 with snap-on cover 323 is connected to the support 320 by suitable means. In the bottom wall 314a of the base there are provided a plurality of upstanding hollow projections 324 aligned with a mating set of projections 326 formed on the lid 312. These projections facilitate stacking of a series of containers in storage. Positioned immediately above the base 314 in the illustration of FIG. 14 is a basket 330 having a bottom wall shaped and sloped to fit the bottom wall 314a of the base 314. The basket 330 also includes a series of projections 332 which mate with the projections 324. A plurality of holes 334 permit condensate to drain from the basket. Positioned immediately above the basket 330 is a cover or lid 336 which mates with the periphery of the basket 330.

Also mounted on the base 314 is a resilient gasket 338 which cooperates with the lid and the base to seal the container. As may be seen from FIG. 15, the gasket includes an inner generally vertical surface that tightly engages the wall 314c on the base, while the lower edge of the gasket engages the flange 314d in the base groove. The gasket 338 includes an outer flexible flange-like portion 338a which engages the lid and deforms to provide a sealing surface, as may be seen in FIG. 16.

Within the actuator housing 322 is positioned a lid holding actuator mechanism 340 which includes a balloon-like member 342 comparable to the member 64 shown in FIGS. 4 and 5. The outer end wall 342a of the member 342 includes a centrally located thickened throat 342d which defines a circular opening into the chamber 343. A ring-shaped plug-like element 346 including an outwardly extending flange-like portion 348, having an outwardly facing groove, snaps within the throat 342d in the wall 342a. While the element 346 closes the chamber 343, there is further provided a retaining ring 350, which surrounds the exterior of the throat holding it in tight engagement with the groove in the flange 348.

The actuator mechanism 340 further includes a hollow pin 344 having one end 344a secured to the interior of the plug 346 and a central portion extending through the member 340, out an opening in a throat portion 342c in the other end 342b of the balloon, and through a hole in the support wall 320. The other end 344b of the pin 344 extends into the path of the lid 312 as it is opened and closed. In FIG. 15, the lid is shown being supported on the pin 344 which is supported by the support wall 320. The pin and the support wall 320 are sufficiently rigid to support the lid in cantilever fashion, as shown. The pin, of course, also supports the balloon-like member 342.

The pin end 344a secured to the plug member 346 is open, and thus defines a passage leading to a hole 352 in the wall of the pin that opens to the interior chamber 343. Thus, the chamber 343 is in fluid communication with the exterior of the balloon 342. A thin ring or band 354 surrounds the tube 344 and extends over the opening 352 to serve as a valve. The band 354, like the band 92 in FIG. 4, is made of heat-shrinkable material which, is initially flexible, and which shrinks at a predetermined temperature, and then becomes rigid when the temperature is lowered.

OPERATION OF EMBODIMENT OF FIGS. 14-16

In use, the surgical instruments or other items to be sterilized are placed within the basket 330, with the cover 336 on the basket. The basket is then positioned on the base 314, and the lid 312 placed onto the base with one edge of the lid supported by the pin 344 of the actuating mechanism 340, as shown in FIG. 15. The other side of the lid is, of course, positioned in the groove 314b of the base engaging the gasket 338. The entire container is then lifted by the handles and placed in an autoclave or other sterilizer to be subjected to a sterilizing cycle.

The operation of the actuator mechanism 340 is similar to the valve closing means described above in connection with FIGS. 1-7, when subjected to sterilizing cycles like that shown in either FIGS. 8 and 9. When high-pressure steam is applied to the container, it enters the container beneath the open lid to perform the desired sterilizing function. If any steam is condensed, in striking the colder items in the container, it will flow off the bottom wall 314 towards the gasket 338 and the groove 314b, where it can escape through the drainage holes 316. The high pressure steam also enters the expandable chamber 343 by way of the hollow pin 344 and the valve opening 352. The temperature of the steam will cause the valve element 358 to shrink, closing the opening 352 and capturing a quantity of high-pressure, high-temperature steam within the expandable chamber 343. The steaming phase of the autoclave cycle can continue for whatever duration is desired and the pin 344 will continue to hold the lid 312 ajar, thus assuring that condensate can drain from the container.

When the steaming phase is over and the steam is allowed to escape from the autoclave, the resulting pressure drop within the autoclave causes the steam captured within the chamber 343 to expand the balloon into the shape or condition shown in FIG. 16. As may be seen, the inner end of the throat 342c of the member 342 engages the support 320. Consequently, when the balloon expands, the only direction which it can move is to urge its outer end 342a together with the plug 346, outwardly away from the container lid. Since the pin 344 is secured to the member 346, the expansion of the chamber retracts or withdraws the pin 344 from beneath the lid 312, thus permitting the lid to fall into sealing position on the gasket 338 as shown in FIG. 16. The pin 344 is withdrawn partially into the chamber 343, although as can be seen, the tip of the pin end 344b remains in the support wall 320 to provide support for the actuator mechanism 340. The pin 344 and the member 342 are, of course, constructed to permit the sliding movement of the pin within the member 342 without leakage of the steam from the chamber. Thus, the container will close at approximately the same location on the curves in FIGS. 8 and 9 that the valve will close in the embodiment of FIGS. 1-7. That is, the lid will fall as the pressure is falling within the autoclave.

Also, as in the other arrangement, the gasket 338 will permit vapor to escape from the container if the pressure on the exterior of the container is further reduced, but it will prevent fluid flow from entering the container. When the autoclave is opened and the pressure returns to normal, the lid is tightly kept on the base as the vacuum in the container. The container can be stored in this sterile condition for an extended duration.

When the container is to be opened, a relief valve 360 in the top of the lid 312 may be pulled open to equalize the pressure inside the container with that surrounding the container, thus, enabling the lid to be lifted. Normally, the container will be carried into the room where the contents of the container are to be used. Thus, if the container is filled with surgical instruments, it would be carried into the operating room. The lid would then be removed and the basket 330 would be lifted from the container together with the cover 336 and carried to the sterile operating area. The purpose for the cover 336 is to prevent the possibility of dust or other unsterile material from falling from the lid 312 into the basket 330 when the lid is being removed from the container. The sterile cover 336 is then removed and the sterile instruments removed as needed during the operation.

When the container is to be reused, it is a simple matter to remove the cap 323 from the actuator housing 322 and replace the actuator mechanism 340 with one having a heat-shrink valve 354 which is not yet shrunk on the tube 344.

EMBODIMENT OF FIGS. 17–22

FIGS. 17–22 disclose a portion of a container similar to that shown in FIG. 14 incorporating a different lid holding a release mechanism. A lever 422 is pivotally mounted on the exterior side of a supporting wall 420 connected to a container base 414. More specifically, there is a generally vertically extending pivot pin 424 mounted on the wall 420, and the lever 422 has a pair of lugs 422a receiving the pivot pin 424 to enable the lever to pivot horizontally about the pin 424. The lever is preferably made of a suitable rigid plastic material similar to the container material. On one end 422b of the lever 422 is formed a hinged flange 428 which extends above the support wall 420. On the other end 422c of the lever there is mounted a pin 430 which extends through a hole in the support wall 420. Surrounding the pin 430 is a coil spring 432 with one end of the spring engaging the outer surface of the support wall 420 and the other end of the spring engaging the lever. Consequently, the spring urges the lever into the position shown in FIGS. 17 and 18 with the flanged end of the lever supporting the lid 412. At the same time, the pin 430 is out of the path of the lid. Note also from FIG. 18 that the hinged flange is somewhat higher than the pin.

Extending between the lever and the exterior of the support wall 420 is an inflatable chamber actuator 440, similar to that shown in FIG. 15 but without the pin 344 or similar to the expandable chamber 64 shown in FIGS. 4 and 5. The actuator 440 may be supported by either the lever 422 or the wall 420, or by both. In the arrangement shown, the plug 446 is made of two parts, one part 446a extending through a hole in the lever, and an outer cap 446b threaded onto the part 446a to mount the actuator on the lever.

OPERATION OF EMBODIMENT OF FIGS. 17–22

In use, the container is positioned in a vacuum-type autoclave with the lid 412 supported on the flanged end of the lever as shown in FIGS. 17 and 18. When steam is applied to the container, the temperature responsive valve (not shown in FIG. 17) within the actuator 440 will close, capturing a quantity of high-pressure steam. When the steaming phase is over and the pressure is allowed to drop within the autoclave, the captured steam within the inflatable chamber will expand and pivot the lever against the urging of the coil spring into the position shown in FIG. 19. This movement of the lever withdraws the flanged end of the lever from beneath the edge of the lid as shown in FIG. 20. Thus, the lid starts to fall towards the base. However, the pivoting of the lever which withdraws the flanged end of the lever has moved the pin 430, attached to the other end of the lever into the path of the lid so that the pin supports the lid, as shown in FIG. 20. Note that the lid is still spaced from the gasket 438 so that the container is still not yet closed and no pressure differential is created between the inside and the outside of the container. This, of course, is similar to that in the arrangements of FIG. 1–7 and 14–16 in that the gaskets act as one-way valves when the lid is positioned on the base. However, at the maximum vacuum point in the vacuum cycle the lid is still open; and hence, when the pressure in the autoclave is allowed to increase, the container pressure can rise also. This is in contrast to the earlier arrangements.

As the pressure surrounding the expandable chamber increases, the chamber will contract closer to its original shape as shown in FIG. 21. Thus, the spring returns the lever to the position shown in FIG. 21. This movement retracts the pin from its lid holding position and, at a predetermined point, allows the lid to fall into closed position on the gasket 438, as shown in FIG. 22. The movement of the lever pivots the flanged end of the lever towards the lid; but since that end is hinged and the lid wall is sloped, the end of flange 428 simply flips up harmlessly as shown in FIG. 22. Alternatively, the slope of the lid and the exact configuration of the flange may be arranged such that the flanged end does not interfere with the lid so that the hinging arrangement is not needed.

Thus, with the arrangement of FIGS. 17–22, the lid may be closed somewhere between the maximum vacuum point shown in FIG. 8 and the ambient pressure line 104. The exact location may be precisely determined and easily modified in selecting the length of the retaining pin. For example, the pin may be threadably mounted in the lever and adjusted inwardly or outwardly. In otherwords, the extent of the vacuum within the closed container may be easily controlled, and this in turn will determine the necessary strength of the container walls. Thinner walls of course require less plastic and hence, are less expensive. As explained above, such an arrangement is practical if the air being introduced into the autoclave to equalize the pressure is suitably filtered so as to be sterile. While present autoclaves do not provide this, future ones may.

What is claimed is:

1. A method of sterilizing and storing items comprising:

placing the items to be sterilized in a container;

placing the container in a sterilizer with the exterior of the container in fluid communication with the interior by having access means to the container being held open by actuator means including an expandable chamber which is initially open to the surrounding environment;

applying a sterilizing environment to the container to sterilize its contents, including applying said environment to the interior of said chamber;

closing said chamber to capture a quantity of said environment in said chamber;

permitting the sterilizing environment to escape or be withdrawn from said sterilizer; and automatically releasing said container access means by utilizing force produced by said expandable chamber as the chamber responds to pressure changes in the environment applied to the container, to thereby close the container before it is subjected to an unsterile environment.

2. The method of claim 1 wherein said sterilizing environment is high pressure steam and the steam captured within said chamber expands the chamber when the pressure surrounding the chamber is lowered.

3. The method of claim 2 wherein said steam is captured within said chamber by closing a valve in response to the temperature of said steam.

4. Apparatus for containing items while being sterilized or stored comprising:

means defining a closed container;

means for permitting access to the container interior;

means mounted on said container holding said access means in an open position; and expandable chamber means for capturing a quantity of a sterilizing environment applied to said container, said chamber means with its captured environment being responsive to a subsequent environment applied to said container for moving said holding means to release said access means and allow the access means to close at a predetermined point in a sterilizing cycle applied to the container.

5. The apparatus of claim 4 wherein said means for capturing a quantity of environment within said chamber means includes valve means responsive to the temperature of said environment.

6. The apparatus of claim 4 wherein said container includes a base and a lid, said lid forming said access means, and said base having structure for supporting said holding means in position to hold said lid in the open position, said expandable chamber means being supported on said holding means, the expandable chamber means reacting against said support structure to withdraw said holding means from supporting said lid at said predetermined point.

7. Apparatus for containing items while being sterilized or stored comprising:

a base and a lid forming a container;

means mounted on said base holding said lid in an open position spaced from said base;

expandable chamber means supported on said holding means responsive to an environment applied to said container for moving said holding means to release said lid and allow the lid to close at a predetermined point in a sterilizing cycle, said chamber means including a wall reacting against a portion of said container to withdraw said holding means from supporting the lid.

8. The apparatus of claim 7 wherein said holding means comprises a pin which in one position supports said lid in an open position, said pin being connected to said expandable chamber means in a manner such that said pin will be moved from its holding position by said expandable chamber means at said predetermined point.

9. The apparatus of claim 8 wherein said pin is attached to one end of said expandable chamber means, extends through said chamber means and slidably through an opening in the opposite end of said chamber means, and said opposite end of said chamber means is confined against a surface of said container so that when the chamber means expands, said one end of said chamber means moves, withdrawing said pin further into the chamber means and thereby withdrawing the pin from its position holding said lid.

10. The apparatus of claim 7 including valve means on said chamber means for permitting environment applied to said container to enter said expandable chamber means; and means responsive to said environment for automatically closing said valve means.

11. The apparatus of claim 10 wherein said holding means comprises a pin which in one position supports said lid in an open position, said pin being connected to said expandable chamber means in a manner such that said pin will be moved from its holding position by said expandable chamber means at said predetermined point, wherein said pin is hollow on one end and said valve means includes an opening in the side of said pin which opens to its hollow interior and to the interior of said expandable chamber means so that environment applied to the exterior of the expandable chamber means can enter the interior of said chamber means by way of said pin and said valve opening.

12. The apparatus of claim 10 or 11 wherein said valve means includes a temperature responsive means for closing said valve means.

13. The apparatus of claim 7 wherein said base includes a portion forming the bottom wall of the container, said bottom wall being raised in its central portion such that the liquid forming on said bottom wall flows by gravity to the periphery of said base, said base further including a groove formed on its periphery for receiving a gasket and said lid to hermetically seal the container.

14. Apparatus for containing items being sterilized or stored comprising:

means defining a container comprising a generally flat base and a lid including a top wall and side walls which cooperate with the periphery of said base to form the container said base further including an upwardly extending portion formed on its periphery positioned outwardly from said lid; and an actuator mechanism including a holding pin supported through a hole in said base portion and extending into the path followed by said lid when the lid is moved into its closed position on the base, said pin being located to hold one side of the lid spaced from the base, said actuator mechanism further including means forming an expandable chamber having a pair of opposing end walls with one of said end walls having an opening therein slidably receiving said pin into the interior of the expandable chamber, said one end wall being positioned adjacent said base portion said pin being secured to the other end of said expandable chamber so that when the chamber expands, said other end of the chamber moves outwardly away from said base portion withdrawing said pin from its position holding the lid away from the base and thus allowing the lid to fall into closed position on said base.

15. Apparatus of claim 14 wherein:

said pin has an opening therethrough that places the interior of the chamber in communication with the exterior of the chamber so that when a sterilizing environment, such as steam, is applied to the exterior of the container and the expandable chamber, it is also applied to the interior of the expandable chamber; and further including valve means responsive to said environment for automatically closing said opening leading into the interior of the expandable chamber to thereby capture a quantity of the sterilizing environment within the expandable chamber.

16. The apparatus of claim 15 wherein said valve means is temperature responsive to close when subjected to steam to thereby capture a quantity of steam within the expandable chamber, said expandable chamber being constructed such that when a quantity of high-pressure steam is captured within the chamber and the pressure surrounding the chamber is reduced, the chamber will expand to cause said pin to be retracted.

17. Apparatus for containing items while they are being sterilized within an autoclave which provides a sterilizing cycle that includes a pressurized steam phase followed by a final vacuum and a return to ambient pressure, comprising:
means defining a container including access means to the container which is open during said steam phase so that steam can enter the container; and
means for automatically closing said access means at a predetermined point in the sterilizing cycle after the maximum vacuum point has been reached in the final vacuum phase of the cycle but before the pressure has returned to ambient pressure, said closing means including an expandable chamber in which is captured a quantity of the steam applied to said container, and said closing means further including means connected to said access means and moved by forces produced by said chamber in response to changing pressures applied to the exterior of the chamber to cause said access means to close.

18. The apparatus of claim 17 wherein said closing means includes a temperature responsive valve which is initially open but closes in response to steam temperature, that controls flow of steam into said chamber.

19. The apparatus of claim 17 wherein said means connected to said access means includes a pivotally mounted lever connected to means for holding the access means open, and said expandable chamber is positioned to cause or permit movement of said lever.

20. The apparatus of claim 19 wherein said expandable chamber is positioned to move said lever to withdraw one end of the lever from holding said access means open while moving the other end of said lever in position to hold said access means open, said expandable chamber further being responsive to an increase in pressure around the chamber to cause the chamber to contract, and including a spring for urging said lever against the force produced by said chamber thereby moving said lever to release said access means as said expandable chamber contracts.

21. Apparatus for containing items while being sterilized or stored comprising:
means defining a container including a lid and a base having mating peripheral portions; and
a lever pivotally supported on said base at a point intermediate the ends of the lever so that opposite ends of the lever can be moved toward and away from said base as the lever pivots;
first means attached to one end of said lever extending into the path of said lid to hold one edge of the lid spaced from the base in one position;
second means connected to the other end of said lever and movable into a closing path of said lid to hold said lid edge spaced from the base in a position lower than said one position;
spring means urging said lever into the position wherein said first holding means is in the path of said lid; and
an actuator responsive to the environment applied to said container, said actuator being positioned to pivot said lever against the urging of said spring to withdraw said first holding means out of the path of said lid and to simultaneously move said second holding means into the path of said lid, whereby said lid will fall from said first holding means onto said second holding means, said actuator being further responsive to said environment to permit said spring to later pivot said lever to withdraw said second holding means from supporting said lid and thereby allowing the lid to fall into closed position on said base.

22. Apparatus for containing items while being sterilized or stored comprising:
means defining a container including a lid and a base;
a lever pivotally mounted on the exterior of the base;
first and second lid holding means connected to opposite ends of said lever;
spring means urging said lever to pivot so that said first lid holding means extends beneath the edge of the lid to hold the lid in open position spaced from the base;
actuator means responsive to the environment applied to said container supported on said container in a position to urge said lever to pivot in opposition to the urging of said spring so that said second lid holding means is urged into the path of said lid to hold the lid spaced from the base, said first holding means being at an elevation higher than said second holding means, said lid being released from said first holding means upon movement of said actuator means in response to environment applied to said container to withdraw said first lid holding means, thus allowing said lid to fall onto said second holding means, said spring being sufficiently strong to pivot said lever to withdraw said second holding means when said actuator means no longer opposes the spring.

* * * * *

UNITED STATES PATENT AND TRADEMARK OFFICE
CERTIFICATE OF CORRECTION

PATENT NO. : 4,247,517
DATED : January 27, 1981
INVENTOR(S) : Roger S. Sanderson et al.

It is certified that error appears in the above-identified patent and that said Letters Patent are hereby corrected as shown below:

On the cover sheet in the Notice regarding the disclaimer, the date specified should be April 17, 1996.

On the cover sheet in the Related U.S. Applications Data, after " Oct. 20, 1976, abandoned" insert --in favor of continuation application Ser. No. 923,359, filed July 10, 1978- and after "Dec. 15, 1975, abandoned" insert --in favor of continuation application Ser. No. 827,992, filed Aug. 26, 1977 now U.S. Patent 4,149,650."

Signed and Sealed this

Seventeenth Day of August 1982

[SEAL]

Attest:

*Attesting Officer*

GERALD J. MOSSINGHOFF
*Commissioner of Patents and Trademarks*